United States Patent [19]
Mandel et al.

[11] 3,951,261
[45] Apr. 20, 1976

[54] NEEDLED SUTURE MOUNTING AND DISPENSING DEVICE AND PACKAGE

[75] Inventors: Harvey B. Mandel, North Brunswick; Eberhard Heinrich Thyen, Middlesex, both of N.J.

[73] Assignee: Ethicon, Inc., Somerville, N.J.

[22] Filed: Aug. 28, 1974

[21] Appl. No.: 501,372

[52] U.S. Cl. ............................ 206/227; 206/370; 206/380; 206/477
[51] Int. Cl.² ................ A61L 17/06; B65D 73/00; B65D 85/24
[58] Field of Search ................ 206/63.3, 363, 370, 206/380, 381, 382, 383, 227, 477, 478, 479, 481

[56] References Cited
UNITED STATES PATENTS

| | | | |
|---|---|---|---|
| 1,387,839 | 8/1921 | Davis | 206/370 |
| 3,136,418 | 6/1964 | Stacy et al. | 206/63.3 |
| 3,202,273 | 8/1965 | Riall | 206/63.3 |
| 3,208,590 | 9/1965 | Blish | 206/478 |
| 3,696,920 | 10/1972 | Lahay | 206/370 |
| 3,779,375 | 12/1973 | Foster | 206/63.3 |
| 3,819,039 | 6/1974 | Erickson | 206/227 X |
| 3,861,521 | 1/1975 | Burtz | 206/63.3 |
| 3,876,068 | 4/1975 | Sonnino | 206/227 |

*Primary Examiner*—Leonard Summer
*Attorney, Agent, or Firm*—Wayne R. Eberhardt

[57] ABSTRACT

A needled suture mounting and dispensing device comprising a separable needle mount and a carrier therefor is described. The needle mount comprises a three-dimensional needle retaining means having a support portion and the carrier comprises a flat card member. Separability of the needle mount from the carrier is achieved either by having the needle mount and carrier as separate members which are fitted together or by having the needle mount be a detachable portion of the carrier. In a preferred embodiment, the needle mount and carrier are two separate members. In this embodiment, the carrier is provided with a pair of parallel slits forming a tongue and slot. The slits are spaced apart at a distance smaller than the width of the support portion of the needle mount and is adapted to receive the needle mount between the tongue and edges of the slot. A package, especially for microsutures, which employs the mounting and dispensing device is also described.

19 Claims, 10 Drawing Figures

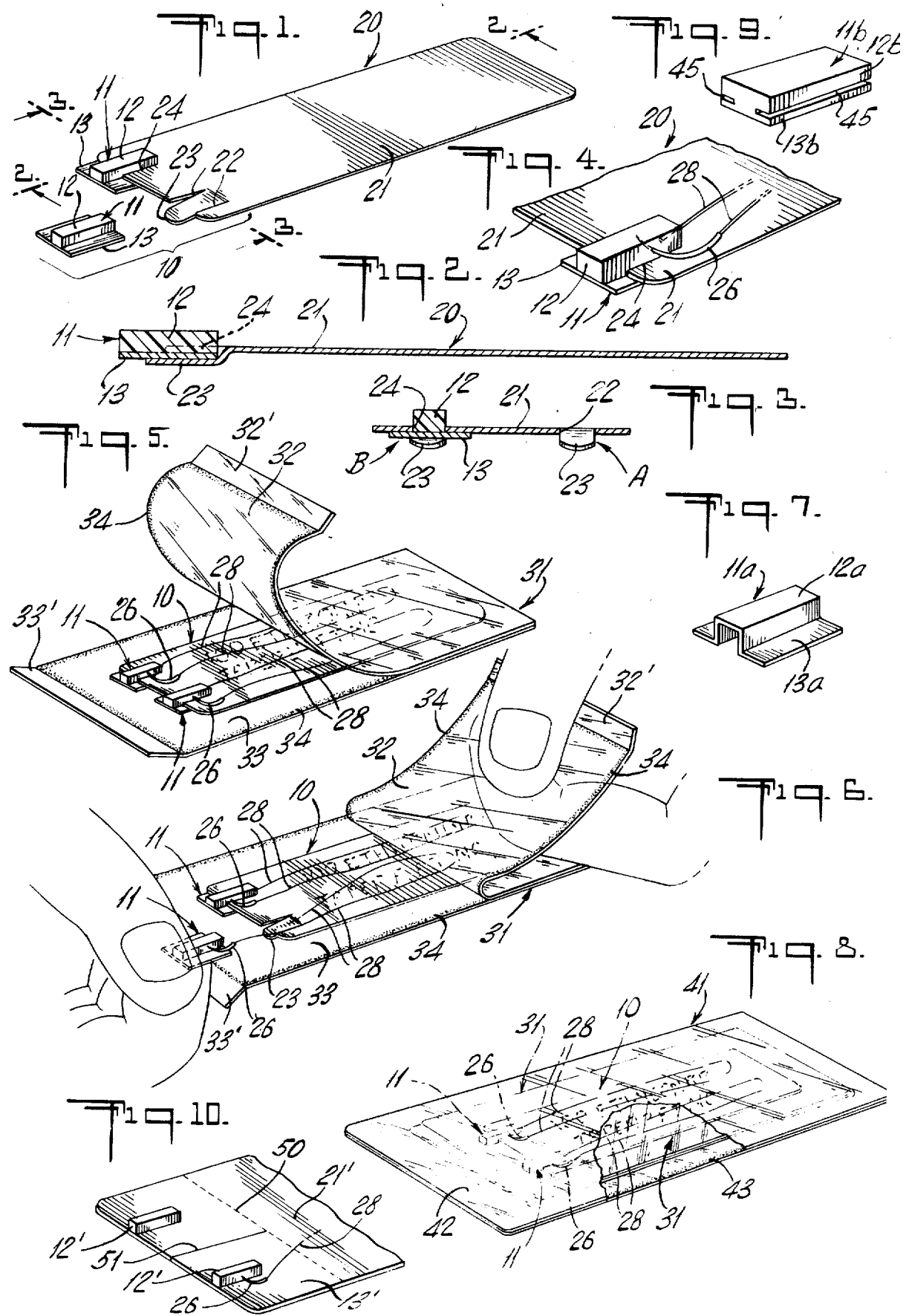

NEEDLED SUTURE MOUNTING AND DISPENSING DEVICE AND PACKAGE

The present invention relates to sterile surgical suture packages and particularly to a device for mounting and dispensing needled sutures, especially microsutures.

In surgical situations, such as cataract surgery, repair of corneal lacerations, and in other instances of opthalmic and vascular surgery where the area of repair is small, where appearance is of special importance or where tolerance by the patient of foreign matter is small, exceedingly fine sutures must be employed. Such sutures are generally referred to as microsutures and as herein employed by the expression "microsuture" is meant a fine needled suture normally employed under magnification. The needles of such microsutures are of wire thickness of 8 mil or finer and the suture strands are of a size corresponding to U.S.P. diameter classification 8-0, 9-0, 10-0, and finer. Although microsutures are employed during the actual suturing process under magnification, preliminary handling such as removal from the package, unwinding the suture strand, transfer of suture, picking up of the needle, etc. is carried out under normal visual conditions. Microsutures, although sometimes visible when immobile and against a contrasting background, readily become difficultly locatable during the preliminary handling. Moreover, locatability is not solely a problem during use, but also during packaging in manufacture. Thus, it is desirable that microsutures be packaged in a way so that it is readily locatable, and particularly in a manner so that it may be dispensed without loss of visual contact.

Because of the fineness and delicate nature of microsutures, conventional ways and conventional sizes for mounting, packaging, and dispensing sutures frequently give rise to unexpected problems. Generally, the dimensions of carrier cards or panels used as supports for the suture in suture packages are from about ¾ to 2 ½ inches in width to about 2 ¼ to 3 inches in length. Normal suture needles are readily removed from these carrier cards. However, microsutures, because of their delicate and fine nature are not readily grasped from these carrier cards whether or not the needle is mounted or held in position in some way. Even when grasping can be achieved, it is difficultly attained and not infrequently the needle is bent in the process. The card interferes in the manipulative process of grasping and recovering the microsuture without damage from its surface.

Problems sometimes associated with packaging, dispensing and use of conventionally sized sutures or microsutures such as kinking of the suture, entanglement of the suture and in the case of certain suture materials, retention of configuration in which the suture had been arranged in the package, frequently also occur with microsutures. Since packaging of microsutures is more difficult, solutions applicable to macrosutures have not always been applicable to the packaging of microsutures. Moreover, when problems do arise, it becomes considerably more troublesome. Existing packages for microsutures have not solved the foregoing problems.

The present invention is directed to a device for mounting and dispensing needled sutures, especially microsutures, and includes an improved package containing needled sutures mounted on said device. The device for mounting and dispensing needled sutures comprises a separable needle mount and a carrier therefor. The needle mount and carrier are preferably two separate members which coact to perform the mounting and dispensing function, but may be a single unit in which the needle mount portion is detachable from the carrier portion.

The preferred device for mounting and dispensing needled sutures of the present invention is a two-member device which comprises (a) a needle mount comprising a three-dimensional needle retaining means and a support therefor which may be an extension of the three-dimensional body or separate piece which is secured to the body, and (b) a carrier for the needle mount comprising a flat member or card which is provided at one end with at least one pair of parallel slits which form a tongue and slot. The needle mount fits between the tongue and slot and is held in place by the tongue and the sides of the slot acting in opposite directions on the support portion of the needle mount. A microsuture when mounted on the device has the needle imbedded in the three-dimensional needle-retaining means of the needle mount, the suture strand looped on the surface of the carrier and the trailing suture end or trailing loop may be retained or sandwiched between the needle mount and tongue of the carrier. Thus, the needle and suture are clearly visible, free from kinking or from retaining a tight configuration, yet also free from entanglement by having the suture end held in place.

When it is desired to take up the suture for use, the needle mount may be picked up by the support and withdrawn from the carrier and thereafter, the needle withdrawn from the needle retaining means. Similarly, when the needle mount is a detachable portion of the carrier, it may be pulled away from the carrier and the needle then withdrawn from the needle retaining means. Because of the small dimensions of the support, the needle may be readily withdrawn from the needle mount with a needle holder without an interfering card or carrier panel. This is especially important in the very finest microsuture where a slight restriction in freedom of movement may result in bent needles. Optionally, with larger needles, the needle mount may be left in the carrier and the needle withdrawn from the needle mount. When the needle is withdrawn, the suture hangs freely without kinks, entanglements, or coils and is ready for use.

In a preferred embodiment, the needle retaining means is made of a transparent material so that the needle is completely visible at all times.

An aspect of the present invention is a complete suture package employing the microsuture mounting and dispensing device of the present invention. The package contemplates complete visibility of the microsuture at all times, from before the package is opened to the final suturing step and is especially valuable for packaging sutures in which moisture sensitivity is not a problem. In such a package, the mounting and dispensing device employs a transparent material for the needle retaining means above described. The mounted and arranged microsuture is packaged in a hermetically-sealed inner and outer envelope which have a transparent top panel. In such package, the location of the needle is known at all times and mishandling is avoided and dispensing is facilitated.

The objects and advantages of this invention will be more readily apparent from the following description and accompanying drawings which illustrate the preferred embodiments of the present invention:

FIG. 1 is a partially exploded view in perspective of a device for mounting and dispensing microsutures according to a preferred embodiment of this invention.

FIG. 2 is a somewhat enlarged view, in section, taken along the Line 2—2 of FIG. 1.

FIG. 3 is a somewhat enlarged view, partly in section and partly in elevation taken along the Line 3—3 of FIG. 1.

FIG. 4 is a fragmentary perspective view showing an enlarged portion of the device of FIG. 1 with the arrangement of the needle and suture end.

FIG. 5 is a view in perspective of a partially opened microsuture package.

FIG. 6 is a view in perspective similar to FIG. 5 of a partially opened microsuture package with the needle mount being removed from its carrier.

FIG. 7 is a view in perspective of another version of a needle mount.

FIG. 8 is a view in perspective of a doubly wrapped complete microsuture package partially broken away to show the inner envelope and its contents.

FIG. 9 is a view in perspective of still another version of a needle mount.

FIG. 10 is a view in perspective of another version of a device for mounting and dispensing microsutures.

Referring to FIGS. 1–4 of the drawings, there is shown a microsuture retaining and dispensing device 10 comprising a needle mount 11 having a three-dimensional needle retaining means 12 and a support 13, and a carrier 20 for the needle mount consisting of a flat member or card 21 slitted at one end by at least one pair of parallel slits 22 which extend inwardly from the outer edge of the card form a tongue 23 and slot 24. The tongue 23 is attached to the flat member or card 21 at the inner ends of the slit 22 and is adapted to be depressed to slideably receive the needle mount 11. It is preferred that the tongue 23 extend slightly beyond the straight edge of card 21 as seen in FIG. 1. This is of added convenience for the inserting or positioning of the needle mount during manufacture. As seen in FIG. 1, the width of the support portion 13 of the needle mount is greater than the distance between the two parallel slits 22 while the width of the three-dimensional needle retaining means 12 is narrower than the distance between the slits and fits in the slot formed by the slits. When the tongue 23 is depressed, the needle mount 11 is inserted into the slot formed by the depressed tongue and held in place by the edges of the slot 24 and the tongue 23. This can be seen further in FIGS. 2 and 3. FIG. 2 shows the tongue 23 below support 13 of the needle mount and one edge of the slot 24 above support 13 is viewed from the side. FIG. 3 is an end view showing at A, the tongue 23 formed by the slits 22 before insertion of the needle mount, and at B, the needle mount in place with the needle retaining means 12 in the slot 24 with the support 13 of the needle mount being held in place by the tongue 23 and the edges of the slot 24. Moreover, as seen in FIGS. 1 and 4, the needle mount when in position, preferably projects or extends slightly beyond the edge of the carrier. This is desirable to facilitate grasping of the needle mount.

As seen in FIG. 4–6, a microsuture is retained on the device of the present invention by imbedding or inserting the tip or point of the needle 26 in the needle retaining means 12 of the needle mount, allowing the suture strand 28 to fold or loop loosely on the flat surface of the card 21 of carrier 20, and securing the free end of the suture strand by retaining it in a recess area formed between the tongue 23 and the support 13 of the needle mount. FIG. 4 shows in detail the needle 26 affixed in the needle retaining means 12 and the suture 28 retained in the recess area. More than one needle may be retained on a single mount, but is less desirable. For double-armed sutures, a pair of needle mounts with a needle in each retaining means is desirable. Since in such sutures there would be no free end, the suture strand may be freely looped on the surface of the carrier card or in the case of long strands, may be held near its midpoint by extending it into a recess area between the two slots and held secure between the flat member portion between the tongues and needle mount support (not illustrated).

The needle-retaining means 12 is a three-dimensional body, preferably a block which protectively secures the needle by the point of the needle being inserted or imbeded therein. Although the exact dimensions are not critical, it should be of sufficient thickness not only to permit insertion of a needle along the thickness, but to provide space around the shaft of the needle for added protection against bending of the shaft in the package. The exact shape of the needle-retaining means is not critical, provided it is of adequate thickness. A rectangular block is convenient and preferred. It is desirable to have a thickness of from about 0.040 to about 0.080 inches. The insertion or imbedding may be accomplished by having the needle pierce the retaining means during mounting or by providing the retaining means with a slit or orifice into which the needle point may be positioned. In either case, it is desirable that the material chosen for the retaining means have resilient properties, namely, such that the adjacent surfaces tend to close in on the needle to hold it in place and still have qualities or releasability on the application of a pulling force. Moreover, if the needle is to be mounted by piercing, the retaining means should be of sufficient softness that it is pierceable without bending or breaking the needle. These desirable combination of characteristics are not necessarily defineable by measurable physical constants. The chemical nature of the material is not critical. Thus, its normal classification may be as a plastic or as an elastomer, etc., and may be an organic or semi-organic polymer. Suitable polymeric materials for the needle mount includee silicone rubber, silicone foam, polyurethane, polystyrene, polypropylene, collagen sponge, nylon, etc. Silicone rubber is the preferred material.

In a preferred embodiment of the present invention, the needle retaining means is of a transparent material, such as for example silicone rubber. When the retaining means is of a transparent material, there is the added advantage of locatability or visibility of the needle which greatly facilitates handling during surgery.

In addition to properties previously enumerated, related to its mechanical function, the material suitable as needle retaining means must have properties consonant with its use as an instrument in surgery. Thus, the material must be of an inert, non-toxic nature to avoid undesirable residues being left on the needle or suture. It should, moreover, be resistant to change under sterilizing conditions. When the needle mount is of a transparent or translucent polymer for the added locatability feature, it should be resistant to discoloration or becoming opaque on sterilization or aging.

In the needle mount 11, the needle retaining means 12 is preferably non-detachably attached or bonded to the support 13 which may be cellulosic or plastic in nature. Generally, a stiff paper or card normally employed in suture packaging is satisfactory for the support. Any suitable means may be employed to attach the needle retaining means to the support. Generally, an adhesive or a double-adhesive tape satisfactorily accomplishes this. It is not necessary, however, that the needle retaining means and the support therefor be of two separate units which are to be attached together. Thus, the needle mount may be of an extrudable or moldable plastic material in which the needle retaining means and the support are portions of a single unit. One such needle mount is illustrated in FIG. 7 where the needle mount 11a has a support portion 13a which is integral with the needle retaining means 12a. Another needle mount in which needle retaining means is an integral part of the support is seen in FIG. 9 where needle mount 11b has a support portion 13b and needle retaining means 12b. It is provided with slits 45 which are adapted to receive the edges of the slot 24.

The carrier 20 is generally also of stiff paper. The dimensions are not critical, but is preferably elongated so that the length is about two to four times the width. In addition to its function as a carrier for the needle retaining means 11 and a support for the suture strand 28, it provides a place for a legend or other printing when the device is employed in a preferred package having transparent top panels as hereinafter described.

Another embodiment of the microsuture mounting and dispensing device is one in which the needle mount is detachably attached to the carrier. One version is seen in FIG. 10 which shows needle retaining means 12' on a support 13' which is detachably attached to card 21'. The line of weakness or perforations which facilitate detachment are seen at 50. When more than one needle mount is contemplated, it may be separated by a slit 51. The device illustrated in FIG. 10 contemplates two needle mounts. Another version (not illustrated) is one in which the needle retaining means is attached to the tongue on the carrier card of the preferred embodiment and perforations or other lines of weakness are provided at the base of the tongue. Other modifications which incorporate detachability are readily apparent to the skilled in the art.

FIG. 5 shows the microsuture mounting and dispensing device 10 in a hermetically-sealed envelope 31 comprising a transparent top panel 32 and a bottom panel 33 which may be opaque. The envelope is sealed around the edge along strip line 34 to provide a hermetically-sealed strippable sterilizable enclosure and may be opened by pulling apart the stripping flaps 32' and 33' which conveniently are extensions of the top panel 32 and the bottom panel 33. The carrier card 21 optionally may be imbedded in the seal at the end opposite opening end. When so imbedded, the needle mount 11 may be removed from the carrier 20 without removal of the entire microsuture mounting and dispensing device from the package as shown in FIG. 6.

The foregoing novel device for mounting and dispensing microsutures when placed in inner or primary and outer or overwrap envelopes which have transparent top panels, provides a novel microsuture package in which substantially the entire microsuture is completely visible from prior to the time the suture package is opened. Such package is seen in FIG. 8 wherein the microsuture mounting and dispensing device 10 is seen wrapped in an inner envelope 31 with a transparent top panel which in turn is wrapped in an outer envelope 41 shown with a transparent top panel 42 and sealing strip 43 along the bottom panels in the broken-away portion. As illustrated in FIG. 8, all components contained in the package is as clearly visible from outside the outer envelope 41 as it is from outside the inner envelope 31 as shown in the portion broken away.

For envelopes of microsuture packages which are to have transparent top panels, the top panel may be a laminate of polyester and polyethylene and the bottom panel may be a laminate of foil and paper held together by an adhesive, preferably of polyethylene. However, other suitable transparent materials may be employed and both top and bottom panels may be transparent. Other suitable transparent materials include polyester-polyolefin, nylon-polyethylene, polypropylene-ionomer (e.g. SURLYN), cellulose acetate-ionomer, etc.

Although the device of the present invention is especially useful in connection with packages employing transparent envelopes, it may also be employed with packages of laminated foil, etc. which are used when moisture impermeability is important.

The mounting and dispensing device of the present invention may be employed in the packaging of both natural or synthetic sutures, absorbable or nonabsorbable. Some specific suture materials applicable in connection with this invention are silk, nylon, polyester, catgut, polypropylene, polyethylene, cotton, linen, homopolymers and copolymers of glycolide and lactide. This invention is, however, not limited to sutures of these materials or to envelopes of materials above described which are listed for illustrative purposes.

The invention is further adapted to be employed using any of the conventional methods of sterilization such as for example radiation, ethylene oxide, etc.

Having described in the invention in specific detail and exemplified in the manner in which it may be carried into practice, it will be apparent to those skilled in the art that innumerable variations, applications, modifications, and extensions of the basic principles involved may be made without departing from its spirit or scope. It is to be understood that the foregoing is merely exemplary and the present invention is not to be limited to the specific form or arrangement of parts herein described and shown.

What is claimed is:

1. A needled suture mounting and dispensing device comprising;
   a. a needle point comprising a three-dimensional, self-sustaining, resilient, pierceable body having support means; and
   b. a carrier for said needle mount comprising a flat card member provided at one end with slot means co-operating with said needle mount support means for receiving and holding said needle mount on said carrier, said needle mount being readily removable from said carrier.

2. A device according to claim 1 comprising a plurality of needle mounts wherein said carrier card is provided with individual receiving means for each needle mount.

3. A device for mounting and dispensing sterile needled sutures comprising:
   a. a needle mount comprising a three-dimensional body mounted on a flat substantially rectangular support of slightly larger flat surface dimensions than that of the three-dimensional body;

b. a carrier for said needle mount comprising a substantially rectangular card provided at one end with at least one pair of parallel slits forming a tongue and slot, said parallel slits being spaced apart at a distance smaller than the width of the flat needle mount support;

wherein said needle mount fits between the tongue and edges of the slot on said carrier.

4. A device according to claim 3, in which the three-dimensional body of the needle mount is of an easily pierceable transparent polymer body.

5. A device according to claim 4, in which the transparent polymer body is of silicone rubber.

6. A device according to claim 3, in which the carrier card is provided with more than one pair of parallel slits.

7. A package for sterile needled sutures comprising at least one sealed envelope having a transparent face and having contained therein at least one needled suture retained on a device for mounting and dispensing needled sutures comprising:
   a. a needle mount comprising a three-dimensional body mounted on a flat rectangular support of slightly larger flat surface dimensions than that of the three-dimensional body;
   b. a carrier for said needle mount comprising a rectangular card provided at one end with at least one pair of parallel slits forming a tongue and slot, said slits being spaced apart at a distance smaller than the width of the flat needle mount support;
   wherein said needle mount fits between the tongue and edges of the slot on said carrier.

8. A package according to claim 6, in which the three-dimensional body of the needle mount is of an easily pierceable transparent polymer body.

9. A package according to claim 6, in which the rectangular card carrier bears printing.

10. A needled suture mounting and dispensing device comprising:
    a. a needle mount comprising a three-dimensional, resilient, rectangular body having carrier accepting slits on two opposing sides; and
    b. a carrier for said needle mount comprising a flat card member provided at one end of a slot, the opposing edges of said slot being spaced to fit the slits of said needle mount and adapted to receive and hold said needle mount on said carrier, said needle mount being readily removable from said carrier.

11. A device according to claim 10 comprising a plurality of needle mounts wherein said carrier is provided with individual slots for each needle mount.

12. A package for sterile needled sutures comprising at least one sealed envelope having contained therein at least one needled suture retained on a device for mounting and dispensing needled sutures comprising:
    a. a needle mount comprising a three-dimensional, self-sustaining, resilient, pierceable body having support means, said needle mount being pierced by and retaining the needle of said needled suture; and
    b. a carrier for said needle mount comprising a flat card member provided at one end with slot means co-operating with said needle mount support means for receiving and holding said needle mount on said carrier, said needle mount being readily removable from said carrier.

13. A package according to claim 12 comprising a plurality of needle mounts wherein the carrier card is provided with individual receiving means for each needle mount.

14. A package for sterile needled sutures comprising at least one sealed envelope having contained therein at least one needled suture retained on a device for mounting and dispensing needled sutures comprising:
    a. a needle mount comprising a three-dimensional resilient, rectangular body having carrier accepting slits on two opposing sides, said needle mount being pierced by and retaining the needle of said needled suture; and
    b. a carrier for said needle mount comprising a flat card member provided at one end with a slot, the opposing edges of said slot being spaced to fit the slits of said needle mount and adapted to receive and hold said needle mount on said carrier, said needle mount being readily removable from said carrier.

15. A package according to claim 14 comprising a plurality of needle mounts wherein said carrier is provided with individual slots for each needle mount.

16. A sterile suture package comprising at least one sealed envelope having a transparent face and having contained therein at least one suture retained on a device for mounting and dispensing needled sutures comprising:
    a. a needle mount comprising a three-dimensional body mounted on a flat substantially rectangular support of slightly larger flat surface dimensions than that of the three-dimensional body;
    b. a carrier for said needle mount comprising a substantially rectangular card provided at one end with at least one pair of parallel slits forming a tongue and slot, said parallel slits being spaced apart at a distance smaller that the width of the flat needle park support;
    wherein said needle mount fits between the tongue and edges of the slot on said carrier; and wherein the tip of the suture needle is imbedded in the needle mount, the suture is looped on the surface of the carrier card and the non-needled end sandwiched between the needle mount and the carrier card.

17. A package according to claim 9, in which the three-dimensional retaining means is made of an easily pierceable transparent polymer material.

18. A package according to claim 9, in which the card carrier bears printing.

19. A package according to claim 9, in which the sealed envelope is contained in a sealed overwrap envelope having a transparent face.

* * * * *

UNITED STATES PATENT AND TRADEMARK OFFICE
CERTIFICATE OF CORRECTION

PATENT NO. : 3,951,261
DATED : April 20, 1976
INVENTOR(S) : Mandel, Harvey B.
Thyen, Eberhard Heinrich It is certified that error appears in the above-identified patent and that said Letters Patent are hereby corrected as shown below:

In column 4, line 46, the word "includee" should read "include".

In column 6, line 50, the word "point" should read "mount".

In column 7, line 44, the word "of" should read "with".

In column 8, line 45, the word "that" should read "than".

Signed and Sealed this

Fourteenth Day of September 1976

[SEAL]

Attest:

RUTH C. MASON
*Attesting Officer*

C. MARSHALL DANN
*Commissioner of Patents and Trademarks*